(12) United States Patent
Lampropoulos et al.

(10) Patent No.: US 7,938,809 B2
(45) Date of Patent: May 10, 2011

(54) QUICK RELEASE HEMOSTASIS VALVE

(75) Inventors: Fred P. Lampropoulos, Salt Lake City, UT (US); Brian W. Stevens, Pleasant Grove, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 53 days.

(21) Appl. No.: 12/102,763

(22) Filed: Apr. 14, 2008

(65) Prior Publication Data
US 2009/0259200 A1 Oct. 15, 2009

(51) Int. Cl.
*A61M 5/00* (2006.01)
*A61M 1/00* (2006.01)
*A61M 25/00* (2006.01)

(52) U.S. Cl. ............... 604/246; 604/30; 604/523

(58) Field of Classification Search .......... 604/246, 604/247, 249, 240, 248, 30, 31, 32, 256, 604/164, 167, 523, 537, 539
See application file for complete search history.

(56) References Cited

U.S. PATENT DOCUMENTS

| | | | |
|---|---|---|---|
| 4,723,550 A * | 2/1988 | Bales et al. ............ | 606/108 |
| 4,857,062 A | 8/1989 | Russell | |
| 4,925,450 A | 5/1990 | Imonti et al. | |
| 4,978,341 A | 12/1990 | Niederhauser | |
| 5,030,206 A * | 7/1991 | Lander ............ | 604/164.12 |
| 5,059,186 A | 10/1991 | Yamamoto et al. | |
| 5,078,688 A | 1/1992 | Lobodzinski et al. | |
| 5,135,492 A | 8/1992 | Melker et al. | |
| 5,195,980 A * | 3/1993 | Catlin ............ | 604/167.04 |
| 5,203,774 A | 4/1993 | Gilson et al. | |
| 5,224,929 A | 7/1993 | Remiszewski | |
| 5,269,764 A | 12/1993 | Vetter et al. | |
| 5,269,771 A | 12/1993 | Thomas et al. | |
| 5,273,546 A | 12/1993 | McLaughlin et al. | |
| 5,324,271 A | 6/1994 | Abiuso et al. | |
| 5,338,313 A * | 8/1994 | Mollenauer et al. ...... | 604/249 |

(Continued)

FOREIGN PATENT DOCUMENTS
WO      WO99/45983      9/1999
(Continued)

OTHER PUBLICATIONS
PCT Search Report and Written Opinion for PCT/US2009/039396 dated Apr. 3, 2009.

*Primary Examiner* — Theodore J Stigell
*Assistant Examiner* — William Carpenter
(74) *Attorney, Agent, or Firm* — Stoel Rives LLP

(57) ABSTRACT

A hemostasis valve apparatus having a quick release apparatus that allows for the exchange of guidewires and other medical instruments into a patient's vasculature while controlling the flow of blood during the exchange. The quick release capability allows tools and instruments to be introduced and removed from the patient's body in a quick and efficient manner without requiring undue attention or manipulation. The quick release capability comprises a lever mechanism which selectively seals or unseals a lumen of the hemostasis valve apparatus. The hemostasis valve apparatus can include a supplemental securement valve assembly which provides a secondary mechanism to secure an instrument positioned in the hemostasis valve and/or control the flow of blood from during the procedure. According to yet another aspect, the quick release mechanism allows for access to the lumen of the hemostasis valve apparatus when the quick release mechanism is in both a released and secured position.

9 Claims, 12 Drawing Sheets

U.S. PATENT DOCUMENTS

| | | | |
|---|---|---|---|
| 5,350,364 A | 9/1994 | Stephens et al. | |
| 5,356,394 A | 10/1994 | Farley et al. | |
| 5,364,371 A | 11/1994 | Kamen | |
| 5,382,230 A | 1/1995 | Bonn | |
| 5,395,349 A | 3/1995 | Quiachon et al. | |
| 5,460,615 A | 10/1995 | Storz | |
| 5,514,109 A | 5/1996 | Mollenauer et al. | |
| 5,542,933 A | 8/1996 | Marks | |
| 5,562,611 A * | 10/1996 | Transue | 604/26 |
| 5,569,208 A | 10/1996 | Woelpper et al. | |
| 5,575,767 A | 11/1996 | Stevens | |
| 5,584,314 A | 12/1996 | Bron | |
| 5,591,137 A * | 1/1997 | Stevens | 604/296 |
| 5,599,327 A | 2/1997 | Sugahara et al. | |
| 5,911,710 A * | 6/1999 | Barry et al. | 604/249 |
| 5,921,968 A * | 7/1999 | Lampropoulos et al. | 604/246 |
| 6,287,280 B1 * | 9/2001 | Lampropoulos et al. | 604/167.03 |
| 6,331,176 B1 * | 12/2001 | Becker et al. | 604/533 |
| 6,458,103 B1 * | 10/2002 | Albert et al. | 604/167.03 |
| 6,572,590 B1 * | 6/2003 | Stevens et al. | 604/246 |
| 6,695,818 B2 * | 2/2004 | Wollschlager | 604/174 |
| 6,986,749 B2 * | 1/2006 | Wollschlager | 600/585 |
| 2007/0106262 A1 | 5/2007 | Becker et al. | |

FOREIGN PATENT DOCUMENTS

| | | |
|---|---|---|
| WO | WO9945983 | 9/1999 |

* cited by examiner

QUICK RELEASE HEMOSTASIS VALVE

BACKGROUND OF THE INVENTION

1. Field of the Invention

The present invention relates to a valve apparatus for use with bloodless exchange of elongate instruments into a patient's vasculature. In more particular, the present invention relates to a valve apparatus having a quick release actuator mechanism which allows the user to quickly and efficiently open and close a seal of the valve apparatus to allow for desired exchange of elongate instruments into the vasculature of a patient.

2. Relevant Technology

Current surgical procedures often require temporary and at times repeated introduction of catheters and/or guidewires into the cardiovascular system of a patient. For example, a catheter can be introduced into the body of a patient and used to deliver fluid, such as a medicament, directly to a predetermined location within the patient's cardiovascular system. Catheters can also be used for exploratory surgery and for removing tissue samples within a body. One primary use of catheters relates to the placement of small angioplasty balloons which can be selectively inflated within a patient's blood vessel to open occlusions within the vessel.

A common catheter design used in performing many procedures includes an elongated, flexible, cylindrical catheter body having a fluid flow passageway or a lumen extending along the interior of that catheter body. In one exemplary procedure, an end of the catheter is inserted into a vessel within the vasculature of the patient. The catheter is advanced along the internal passageway of the vessel until the end of the catheter is located at a predetermined location with the patient's body. The location is often associated with a point at which a medicament is to be delivered or a therapeutic procedure is to be performed.

The long, cylindrical, and rigid but manipulable configuration of common guidewires facilitates directing catheters utilized in such procedures to a desired location within the body. In other words, the rigid configuration and small diameter of such guidewires are specially configured for directing and advancing the guidewire to a desired location within the cardiovascular system. The end of the guidewire, positioned outside the body of the patient, is then received within the lumen of the catheter. Using the guidewire as a guide, the catheter is advanced along the length of the guidewire so as to properly position the catheter within the body of the patient. If desired, the guidewire can then be removed from within the catheter to open the lumen of the catheter. In an alternative process for inserting the catheter, the guidewire is initially received within the lumen of the catheter and the catheter and guidewire are simultaneously advanced within the cardiovascular system of the patient.

Medical procedures which utilize catheters can often require the insertion and removal of several different types of catheters and guidewires. One of the problems encountered with the insertion and removal of catheters and guidewires is controlling bleeding at the point where the catheters and guidewires are first introduced into the cardiovascular system. One approach which has been utilized to control the bleeding at the catheter insertion point while also facilitating insertion and removal of the catheter and/or guidewire within the cardiovascular system is to utilize an introducer during the insertion procedure. An introducer is a relatively large gauge tube which is inserted into the patient. One end of the introducer is positioned outside the body of the patient and is attached to an adapter. The adapter typically comprises a short, rigid tube having a passageway extending therethrough. The adapter tube includes a valve commonly referred to as a hemostasis valve. The hemostasis valve, which either closes independently or is compressed around the catheter and/or guidewire, restricts blood from spilling out of the adapter through the lumen of the valve.

A variety of hemostasis valve apparatus have been utilized in connection with medical insertion procedures. One challenge with many hemostasis valve apparatus relates to sealing and unsealing of the hemostasis valve during insertion and removal of guidewires, catheters and other medical instruments. Traditional hemostasis valve apparatus can require two-handed or other awkward manipulation which can interfere with other aspects of the procedure to be performed. One example of a hemostasis valve apparatus that has been developed to overcome many of the deficiencies of existing hemostasis valve designs is disclosed in U.S. Pat. No. 5,921,968 which is assigned to Merit Medical Systems. The hemostasis valve apparatus provides an adjustable quick-release mechanism which allows a user to seal and unseal the lumen of the seal. Additionally, the hemostasis valve apparatus provides for simple, efficient and one-handed operability which allows the user to selectively release and restore the seal of the hemostasis valve apparatus.

BRIEF SUMMARY OF THE INVENTION

Exemplary embodiments of the invention are directed to a hemostasis valve apparatus having a quick release capability that allows for the exchange of guidewires and other medical instruments into a patient's vasculature while controlling the flow of blood during the exchange. The quick release capability allows guidewires, catheters, and other elongate tools and instruments to be introduced into and/or removed from the patient's body in a quick and efficient manner without requiring undue attention or manipulation during the exchange of such instruments.

According to one aspect of the present invention, the quick release capability comprises a lever mechanism which selectively seals and unseals a lumen of the hemostasis valve apparatus. For example, according to one embodiment the lever arm communicates with a plunger which applies a compressive force to a compressive seal of the hemostasis valve assembly. The lever arm releases pressure from or applies pressure to the plunger and thus to the compressive seal. The compressive seal is positioned in a normally closed position. When the user actuates the lever mechanism, the lumen of the compressive seal opens allowing for the introduction of guidewires, catheters or other elongate instruments through the hemostasis valve apparatus. When the user releases the lever mechanism, the plunger again applies a compressive force to the compressive seal, effectively closing the lumen of the compressive seal. According to yet another aspect of the present invention, the quick release mechanism allows for access to the lumen of the hemostasis valve apparatus when the quick release mechanism is in both a released and secured position.

According to another aspect of the present invention, the hemostasis valve apparatus includes a supplemental securement valve assembly which provides a secondary mechanism to secure an instrument positioned in the hemostasis valve apparatus and/or to control the flow of blood during the procedure. According to one embodiment of the present invention, the supplemental securement valve assembly is integrally coupled to the hemostasis valve apparatus. According to yet another embodiment of the present invention, the supplement securement valve assembly can be selectively secured to the hemostasis valve apparatus.

According to one aspect of the present invention, the seal utilized with the hemostasis valve assembly does not comprise a compressive seal. For example, according to one embodiment of the present invention, the seal comprises a resilient seal. The quick release mechanism controls the advancement and retraction of a dilator which opens and closes the resilient seal.

DETAILED DESCRIPTION

Figure 1:
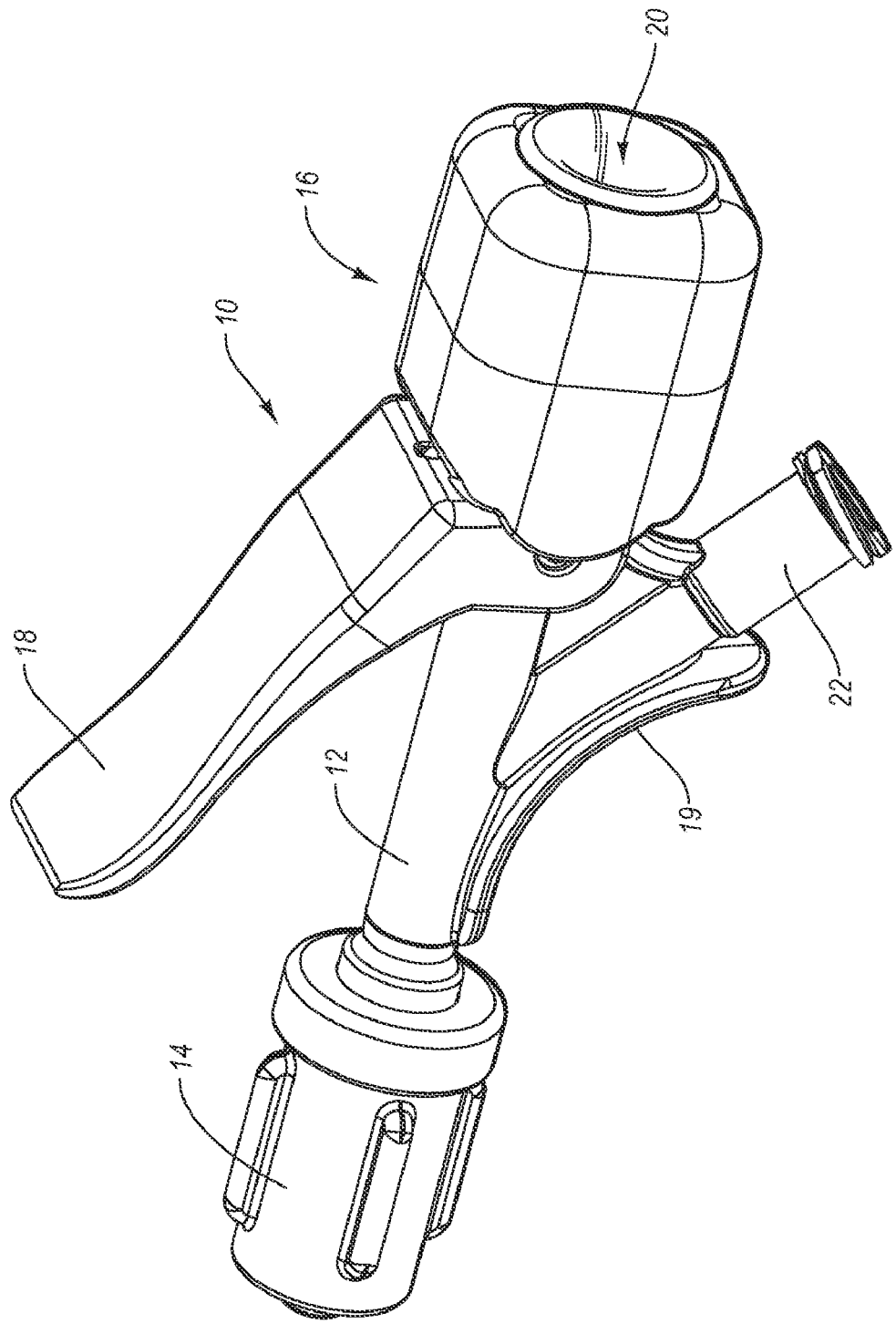
FIG. 1 is a perspective view of a valve apparatus according to one embodiment of the present invention.

FIG. 1 is a perspective view of the valve apparatus 10 according to one embodiment of the present invention. Valve apparatus 10 is configured to be coupled to an introducer sheath in a manner that allows for the exchange of guidewires and other medical instruments into a patient's vasculature while controlling the flow of blood during the exchange. When valve apparatus 10 is coupled to an introducer sheath or other catheter which is positioned within the patient's vasculature, valve apparatus 10 allows guidewires, catheters, and other elongate tools and instruments to be introduced into and/or removed from the patient's body in a quick and efficient manner without requiring undue attention or manipulation during the exchange of such instruments.

In the illustrated embodiment, valve apparatus 10 comprises a tubular body 12, a rotatable connector 14, a valve assembly 16, a lever arm 18, a finger support 19, and a supplemental access port 22. Tubular body 12 comprises the body of valve apparatus 10 and is the member to which the other components of valve apparatus 10 are mounted. Tubular body 12 provides an elongate channel through which guidewires, stents and other medical instruments can be introduced into the patient's body.

Rotatable connector 14 is positioned at the distal end of valve apparatus 10. Rotatable connector 14 provides a threaded coupling by which tools or instruments, such as a dilator, can be coupled to valve apparatus 10. Valve assembly 16 permits a practitioner to selectively actuate between a sealed and an unsealed configuration during the introduction and removal of instruments and tools from valve apparatus 10.

In the illustrated embodiment, lever arm 18 is provided in connection with valve assembly 16. Lever arm 18 can be simply and efficiently actuated by the user to selectively open and close the seal associated with valve assembly 16. Lever arm 18 also facilitates desired gripping of valve apparatus 10 during the introduction of tools and instruments through valve apparatus 10. In the illustrated embodiment, lever arm 18 is pivotably coupled to tubular body 12 in a manner such that when a user actuates lever arm 18 by biasing lever arm 18 in a downward direction, lever arm 18 engages valve assembly 16 effectively opening the seal associated with valve assembly 16. In the illustrated embodiment, lever arm 18 engages valve assembly 16 on the end opposite the access to main lumen 20.

Finger support 19 is positioned on the under side of tubular body 12 such that finger support runs along tubular body 12 and onto the back side of supplemental access port 22. In this manner, a user can grip finger support 19 with one finger while exerting downward pressure on lever arm 18 with the user's thumb. As will be appreciated by those skilled in the art, a gripping surface such as a raised logo, embossed wording or other texturing can be provided on the engagement surface of lever arm 18. The texturing on the engagement surface of lever arm 18 provides a gripping texture minimizing slippage or accidental release of lever arm 18 as it is being held or actuated by a user. A grip surface can also be provided in connection with finger grip 19.

In the illustrated embodiment, main lumen 20 of valve apparatus 10 is accessed through valve assembly 16 and runs the entire length of tubular body 12. Main lumen 20 provides access to the vasculature of a patient either directly or through other medical apparatus to which valve apparatus 10 is coupled. A dilator is one example of a medical apparatus to which valve apparatus 10 can be coupled.

Supplemental access port 22 is provided in connection with valve apparatus 10. Supplemental access port 22 is integrally coupled to tubular body 12. Supplemental access port 22 allows for the introduction of medicaments, tools and instruments, such as a guidewire, into the vasculature of the patient. Additionally, supplemental access port 22 allows for the introduction of medicine, saline, or other fluids into the patient when a tool or instrument is positioned within main lumen 20. According to one embodiment of the present invention, supplemental access port 22 and tubular body 12 comprise a Y-connector body.

As will be appreciated by those skilled in the art, a variety of types and configurations of valve apparatus 10 can be utilized without departing from the scope and spirit of the present invention. For example, according to one embodiment of the present invention, the valve apparatus utilizes a quick release actuator mechanism other than a lever arm. According to another embodiment of the present invention, the quick release mechanism comprises an integral part of the valve assembly. According to yet another embodiment of the present invention, first and second valve assemblies can be actuated by utilizing a quick release actuator mechanism, such as a toggle, lever arm, or the like.

Figure 2:
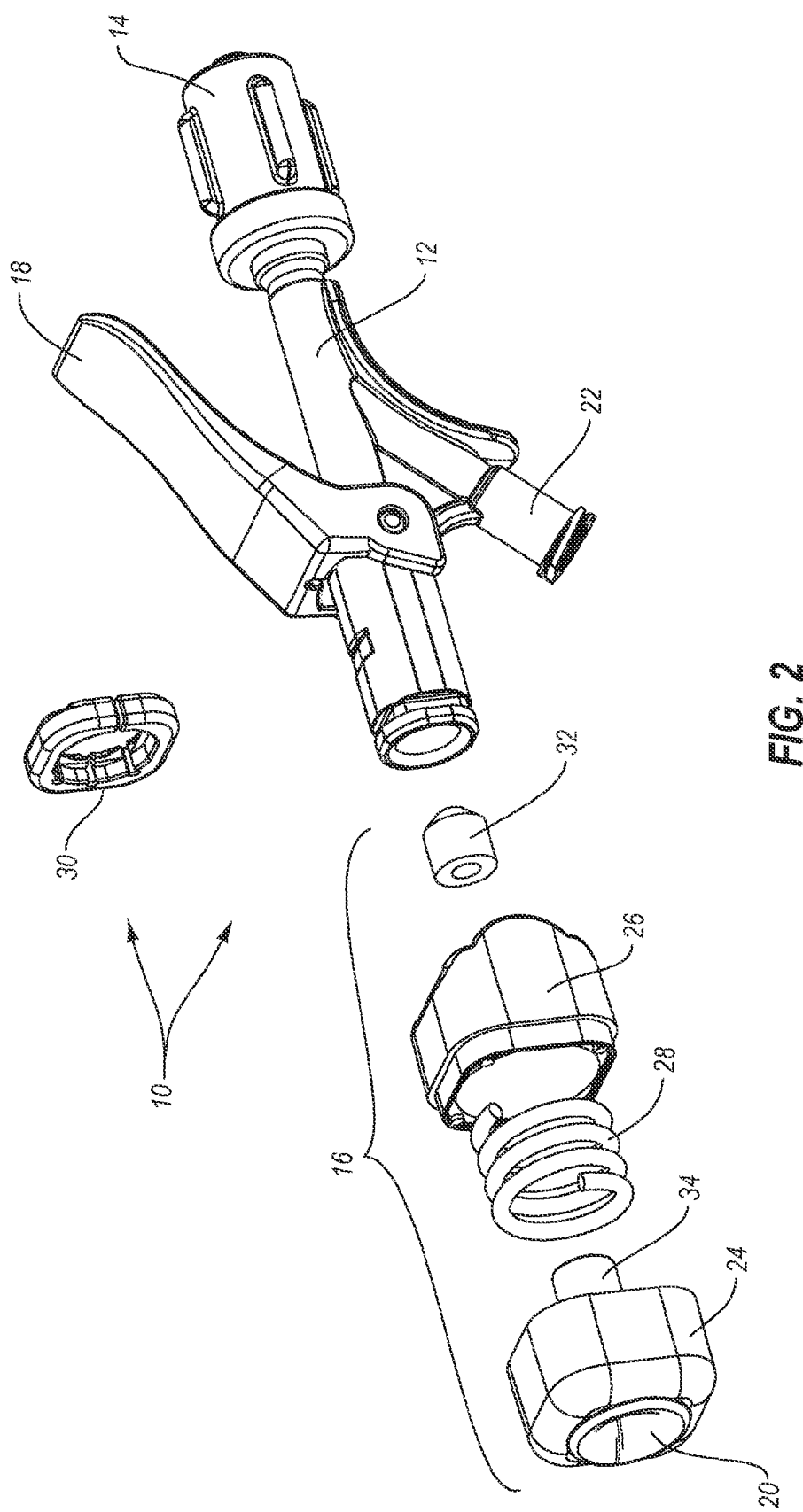
FIG. 2 is an exploded perspective view of the valve apparatus of FIG. 1 illustrating the components of the valve apparatus.

FIG. 2 is an exploded view of valve apparatus 10 illustrating the components of valve apparatus 10. In the illustrated embodiment, lever arm 18 is pivotally coupled to tubular body 12. Lever arm 18 is configured such that as the user exerts a downward force on the distal portion of lever arm 18, the distal end of lever arm 18 moves closer to tubular body 12. As lever arm 18 moves closer to tubular body 12, the angle between lever arm 18 and tubular 12 body becomes smaller. When lever arm 18 is fully depressed, lever arm 18 has moved substantially into alignment with tubular body 12 such that lever arm 18 is substantially parallel to tubular body 12.

In the illustrated embodiment, the components of valve assembly 16 are depicted. Valve assembly 16 comprises an outer housing member 24, an inner housing member 26, a spring 28, a spring retainer 30, and a seal 32. Outer housing member 24 and inner housing member 26 are assembled to form an outer housing of valve assembly 16. The components of valve assembly 16 are configured to be positioned internal to outer housing member 24 and inner housing member 26. In this manner, the components of valve assembly 16 can operate without being displaced or otherwise disrupted in a manner that would interfere with the proper operation of valve assembly 16.

Spring 28 is positioned within an inner chamber formed by the coupling of outer housing member 24 and inner housing member 26. Spring 28 provides a compressive force which is utilized to selectively close seal 32 of valve assembly 16. In the illustrated embodiment, spring 28 comprises a compressive spring which exerts a desired amount of pressure on the components of valve assembly 16 to effectively close seal 32. Seal 32 comprises an annular compressive seal which is positioned within the proximal end of tubular body 12. Seal 32 is positioned within a seat of tubular body 12. The interaction between seal 32 and the seat of tubular body 12 results in the closure of seal 32 when a compressive force is exerted on seal 32 by one or more components of valve assembly 16. When valve apparatus is assembled and lever arm 18 is in a released position, seal 32 is in a normally closed position.

In the illustrated embodiment, a spring retainer 30 is provided. Spring retainer 30 comprises an annular flange which is secured to the distal end of tubular body 12. When spring retainer 30 is secured to the distal end of tubular body 12, the chamber formed by the coupling of outer housing member 24 and inner housing member 26 envelopes spring retainer 30. Spring 28 and inner housing member 26 are positioned such that spring 28 and inner housing member 26 are sandwiched between spring retainer 30 and lever arm 18. In this manner, the compressive force of spring 28 is exerted against spring retainer 30 and inner housing member 26.

Because inner housing member 26 is coupled to outer housing member 24, the compressive force exerted by spring 28 on inner housing member 26 biases outer housing member 24 in the direction of lever arm 18. Plunger 34 of outer housing member 24 is biased in the direction of lever arm 18 as a result of the movement of outer housing member 24. As plunger 34 is biased in the direction of lever arm 18, plunger 34 contacts the proximal end of seal 32 and exerts a compressive force on seal 32. When a threshold amount of force is exerted on seal 32, the compressive force exerted on seal 32 by plunger 34 deforms seal 32 and the lumen of seal 32 is completely occluded. In the illustrated embodiment, spring 28 is positioned around plunger 34. A more complete description of the operation of the components of valve assembly 16 and the juxtaposition of the components of valve assembly 16 relative to the other components of valve apparatus 10 will be provided in greater detail with reference to FIGS. 3 and 4.

As will be appreciated by those skilled in the art, a variety of types and configurations of valve apparatus 10 can be utilized without departing from the scope and spirit of the present invention. For example, according to one embodiment of the present invention, a seal is provided independent of the valve assembly. In another embodiment, the seal is selectively opened but can be closed based on the actuation of a lever arm or similar mechanism. According to another embodiment of the present invention, the valve is normally closed but can be opened upon actuation of the lever arm or a similar mechanism. According to yet another embodiment of the present invention, the forces utilized to actuate the valve assembly are provided by a mechanism other than a spring. According to another embodiment of the present invention, the mechanism for gripping an elongate instrument is separate from the seal mechanism.

Figure 3:
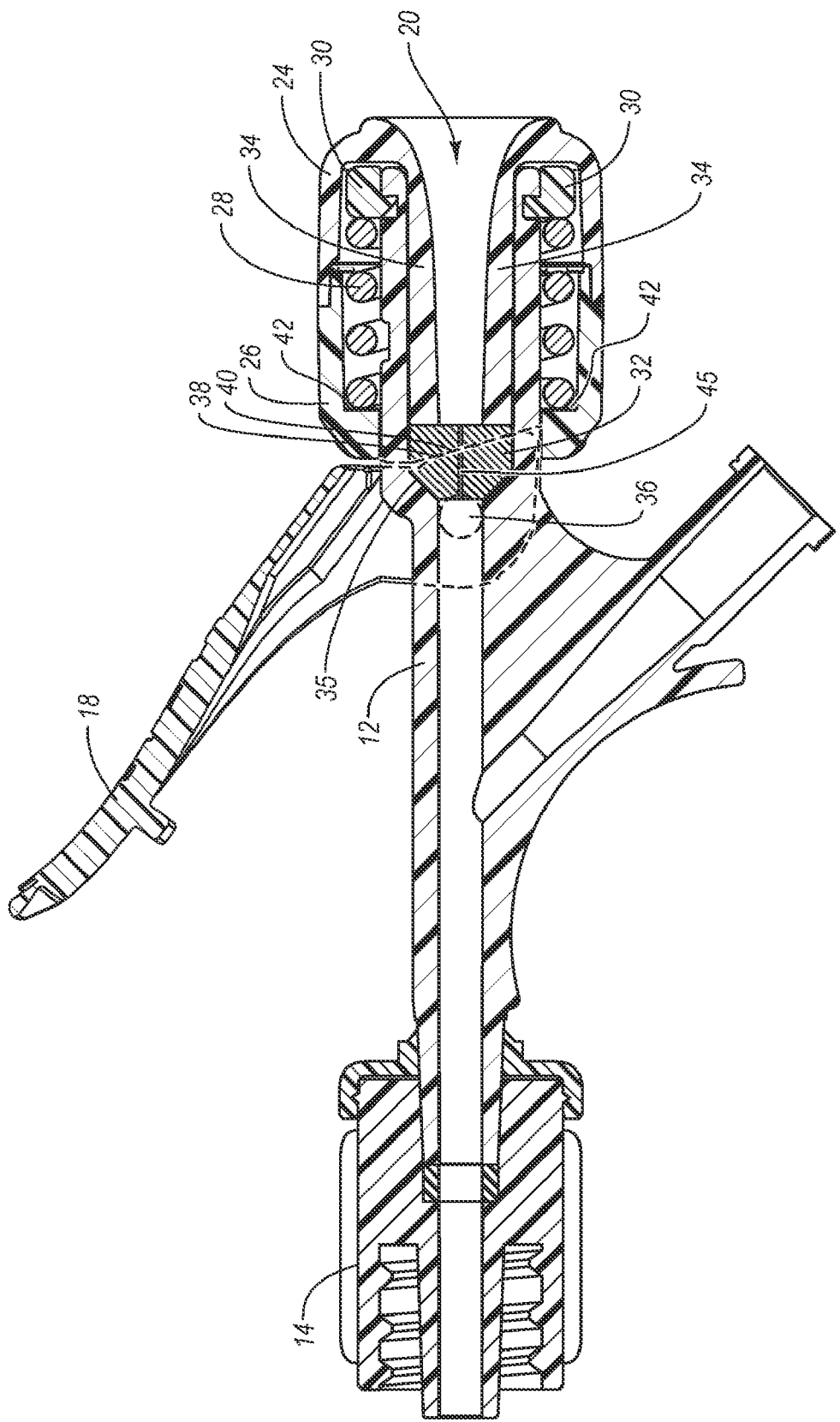
FIG. 3 is a side cross-sectional view illustrating the valve apparatus wherein the quick release actuator mechanism is in a released position.

FIG. 3 is a cross sectional side view of valve apparatus 10 according to one embodiment of the present invention. In the illustrated embodiment, lever arm 18 is released and the components of valve assembly 16 are in a normally closed position. When the components of valve assembly 16 are in a normally closed position, seal 32 is closed and the exchange of fluid through main lumen 20 is prevented. In the illustrated embodiment, the juxtaposition of valve assembly 16 relative to lever arm 18 is depicted.

As previously discussed, valve assembly 16 includes a spring retainer 30. Spring retainer 30 is mounted on the distal end of tubular body 12. Spring retainer 30 comprises an annular flange which provides a contact surface against which the proximal end of spring 28 can abut. Spring 28 is positioned between spring retainer 30 and an annular spring contact surface 42 of inner housing member 26. The compressive forces exerted by spring 28 urges inner housing member 26 in the direction of lever arm 18. Because inner housing member 26 is coupled to outer housing member 24, biasing of inner housing member 26 results in movement of outer housing member 24 in the direction of lever arm 18. In other words, spring 28 is compressed substantially in the same direction as the movement of plunger 28. In this manner, plunger 34 of outer housing member 24 exerts a compressive force on seal 32.

Seal 32 is configured to be positioned in seat 35 of tubular body 12. Seat 35 of tubular body 12 has a tapered configuration. As a result, when plunger 34 contacts the proximal end of seal 32, the interaction of forces between plunger 34 and seat 35 results in compression of seal 32 and closing of the central passageway 45 of seal 32. When a user desires to selectively open seal 32, a user simply exerts a downward pressure on lever arm 18. By exerting a downward pressure on lever arm 18, lever arm 18 is biased such that lever arm 18 rotates about pivot 36. Biasing of lever arm 18 in the downward direction results in the exertion of forces by contact surface 38 of lever arm 18 against ramp surface 40 of inner housing member 26.

Figure 4:
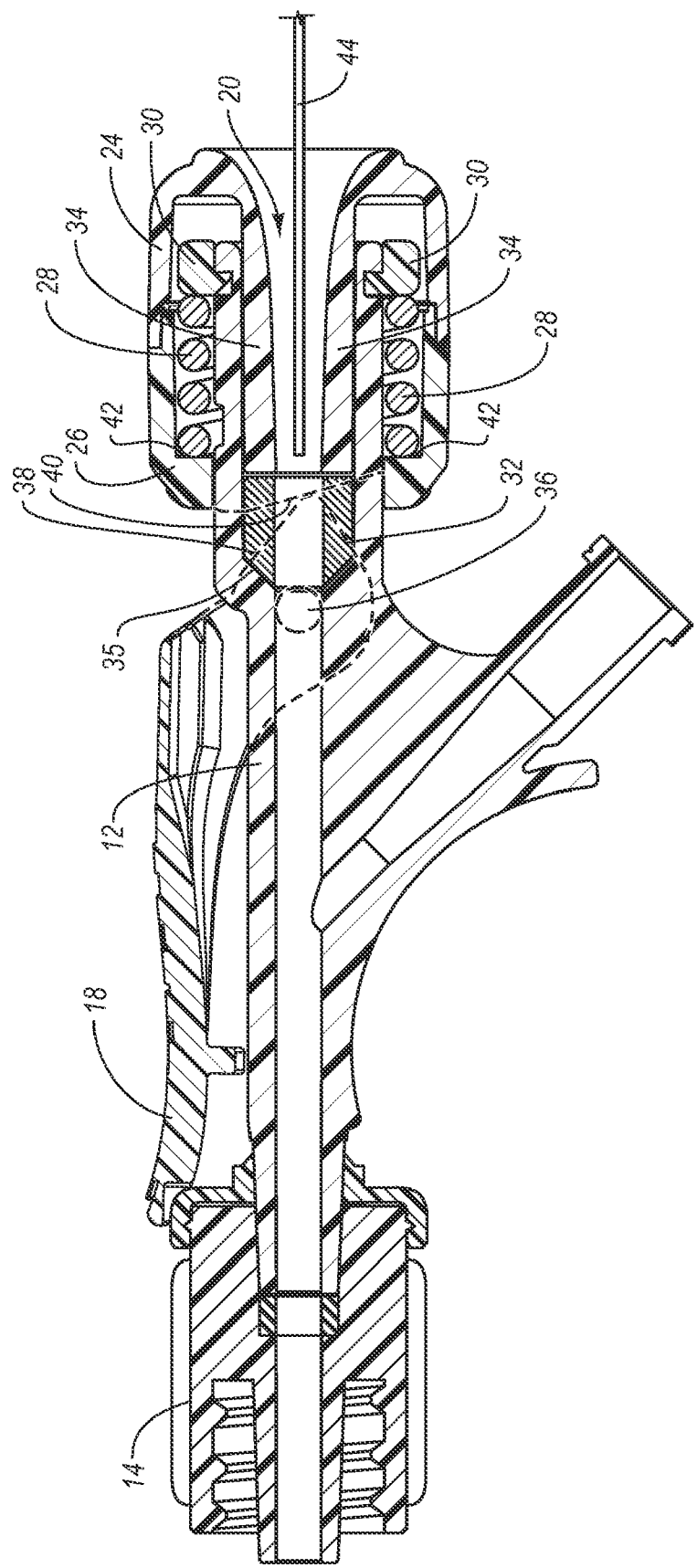
FIG. 4 is a side cross-sectional view illustrating the quick release actuator mechanism in which the lever is in a depressed position and the seal of the valve apparatus is open.

FIG. 4 is a side view of valve apparatus 10 illustrating actuation of lever arm 18. When a user depresses the end of lever arm 18 in the downward direction, the mechanical advantage provided by the juxtaposition of pivot 36, the length of lever arm 18 and the configuration of contact surface 38 facilitates controlled movement of inner housing member 26 in the proximal direction. The fixed coupling of spring retainer 30 to the proximal end of tubular body 12 and movement of inner housing member 26 results in compression of spring 28. As inner housing member 26 moves in the proximal direction, the distance between annular spring contact surface 42 of inner housing member 26 and spring retainer 32 decreases.

As the distance between annular spring contact surface 42 and spring retainer decreases, the spring is compressed and outer housing member 24 and inner housing member 26 are moved proximally relative to tubular body 12. As a result, plunger 34 is also moved proximally such that the distance between plunger 34 and seat 35 of tubular body 12 is increased. As the distance between seat 35 and plunger 34 increases, seal 32 is able to return to a non-compressed configuration in which central passageway 45 of seal 32 is allowed to open. When the central passageway 45 through seal 32 is opened, guidewires and other elongate medical instruments such as instrument 44 can be introduced through main lumen 20. As instruments are introduced through main lumen 20 and through the central passageway 45 of seal 32, the instruments pass from the proximal portion to the distal portion of valve apparatus 10 and then into the patient.

In the illustrated embodiment, an elongate instrument 44 is being inserted into valve apparatus 10. As will be appreciated by those skilled in the art, once elongate instrument 44 is extended through seal 32 of valve apparatus 10, a user can release lever arm 18 allowing the valve assembly to return to the normally closed position as depicted with reference to FIG. 3. As seal 32 closes and as valve assembly 16 returns to its normally closed position, seal 32 closes around the outer circumference of elongate instrument 44 effectively preventing the passage of blood or other fluids from the patient's vasculature to the external environment.

As the user releases the downward forces on lever arm 18, the compressive forces exerted by spring 28 against annular spring contact surface 42 of inner housing member 26 urges inner housing member in the direction of lever arm 18. The configuration of ramp surface 40 allows controlled utilization of the compressive forces exerted by spring 28 on inner housing member 26. In other words, ramp surface 40 provides for in the gradual movement and biasing of lever arm 18 to the raised position as depicted in FIG. 3. The configuration of contact surface 38 of lever arm 18 and ramp surface 40 of inner housing member 26 are configured to provide cooperative interaction which prevents advancement of inner housing member 26 beyond a given point. As a result, further extension of spring 28 is prevented and the desired amount of compressive force on seal 32 is maintained.

As will be appreciated by those skilled in the art, a variety of types and configurations of valve apparatus can be utilized without departing from the scope and spirit of the present invention. For example, according to one embodiment of the present invention, the spring is provided in connection with the lever arm such that the spring forces are exerted directly on the lever arm rather than as a part of the valve assembly. According to another embodiment of the present invention, the housing of the valve assembly is a single-piece component rather than being utilized as two separate parts. According to another embodiment of the present invention, the lever arm exerts forces directly on the plunger. According to yet another embodiment of the present invention, the valve assembly utilizes a non-compressible seal.

Figure 5A:
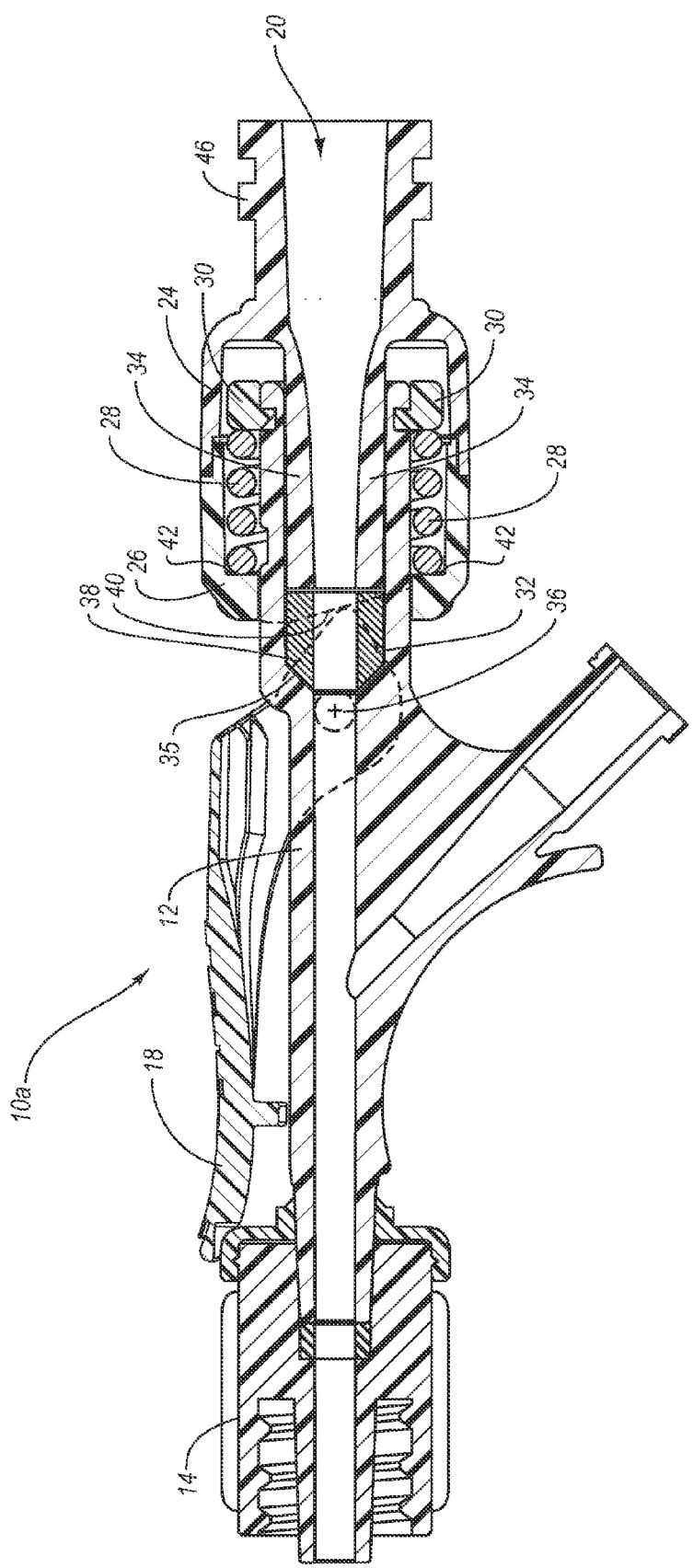
FIG. 5A is a side cross-sectional view of a valve apparatus configured to be utilized with a supplemental securement apparatus.

FIG. 5A is a perspective view of a valve apparatus 10a according to one embodiment of the present invention. In the illustrated embodiment, valve apparatus 10a illustrated in FIG. 5A is configured to be utilized in connection with a supplemental securement apparatus 50 depicted in FIG. 5B. In the illustrated embodiment, valve apparatus 10a is operably similar to the valve apparatus 10 illustrated with reference to FIGS. 1 through 4. Supplemental securement apparatus 50 (see FIG. 5B) can be utilized in connection with valve apparatus 10a to engage an elongate instrument which is positioned in the main lumen 20. By providing a supplemental securement apparatus 50 (see FIG. 5B) in connection with valve apparatus 10a, gripping redundancy of the elongate instrument relative to tubular body 12 of valve apparatus 10a is provided.

In the illustrated embodiment, valve apparatus 10a includes a threaded coupler 46. Threaded coupler 46 is positioned on the proximal end of valve apparatus 10a. Threaded coupler 46 allows supplemental securement apparatus 50 (see FIG. 5B) to be secured to valve apparatus 10a when the supplemental securement apparatus 50 (see FIG. 5B) is helpful to provide supplemental gripping of an elongate instrument.

Figure 5B:
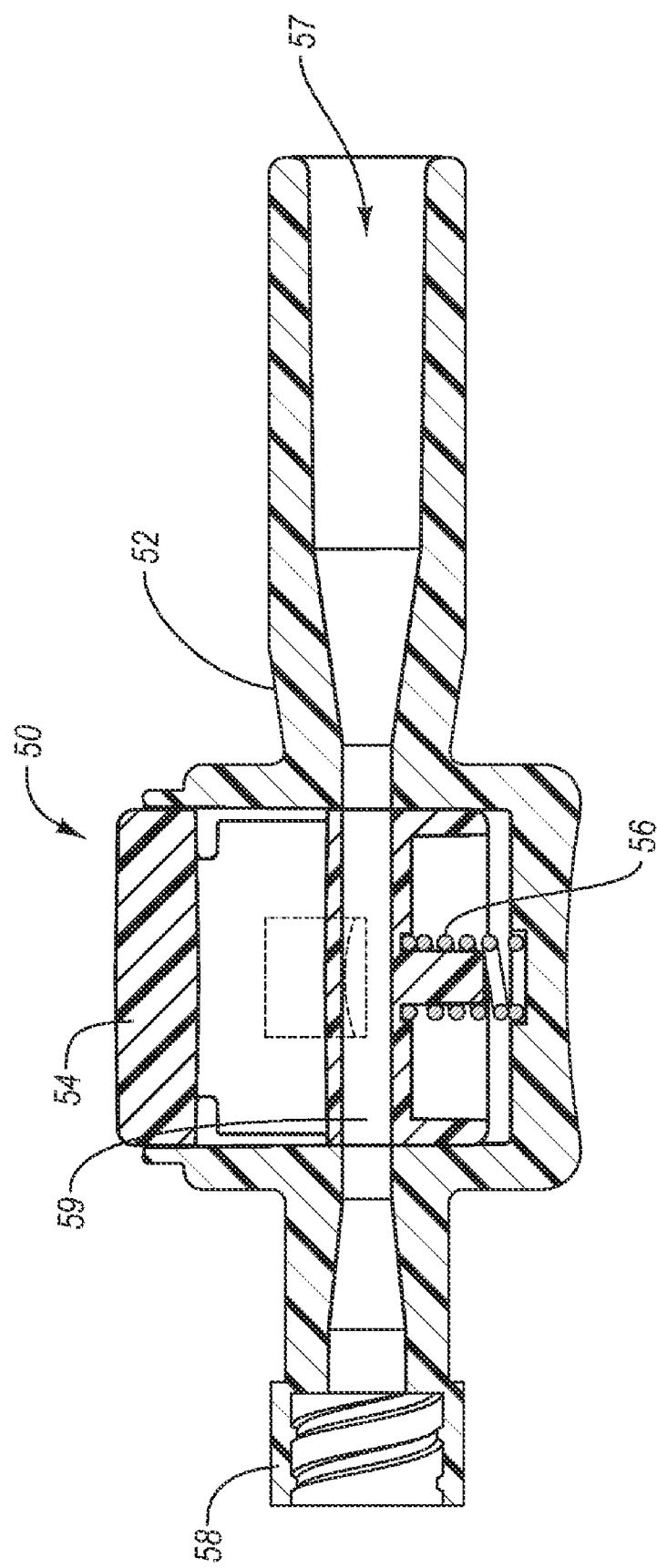
FIG. 5B is a side cross-sectional view of a supplemental securement apparatus configured to be utilized with the valve apparatus of FIG. 5A.

With reference now to FIG. 5B, in the illustrated embodiment, supplemental securement apparatus 50 comprises a body 52, a release button 54, an engagement spring 56, a main lumen 57, and a threaded coupler 58. Body 52 comprises a molded housing to which the other components of supplemental securement apparatus are mounted. A release button 54 is positioned within body 52. Release button 54 allows the user to selectively engage an elongate instrument which is threaded through the main lumen of body 52.

In the illustrated embodiment, release button 54 is positioned in perpendicular relationship to main lumen 57. Main lumen 57 extends longitudinally along the length of body 52. Main lumen 57 is sized to allow elongate instruments to be threaded through valve apparatus 10. An engagement spring 56 is provided in connection with release button 54. Engagement spring 56 exerts a compressive force urging release button 54 upwards relative to main lumen 57. As a result, when a user releases the compressive force exerted on release button 54, the lumen associated with release button 54 moves out of alignment with main lumen 57. As release button moves out of alignment with main lumen 57, the bottom contact surface of lumen 59 is biased in an upward direction. An elongate instrument positioned along the length of main lumen 57 is engaged between the bottom contact surface of lumen 59 and the upper contact surface of main lumen 57. As a result, the elongate instrument is clamped between main lumen 57 and lumen 59 of release button 54. Clamping of main lumen 57 and lumen 59 secures the elongate instrument relative to the supplemental securement apparatus 50.

When a user desires to release the elongate instrument, the user simply depresses release button 54 and then slides the instrument from within the length of main lumen 57. In the illustrated embodiment, supplemental securement apparatus 50 includes a threaded coupler 58. Threaded coupler 58 is configured to threadedly engage threaded coupler 46 of valve apparatus 10a. In this manner, when a user desires to provide supplemental securing to the securement provided by seal 32 of valve apparatus 10a, the user simply threads the elongate instrument along the length of main lumen 57. Once the elongate instrument is threaded along the length of main lumen 57, the user releases compressive forces on release button 54.

As the user releases the downward pressure on release button 54, engagement spring 56 biases release button 54 in the upward direction. When release button moves in the upward direction an elongate instrument can be secured between the bottom contact surface of lumen 59 and the upper contact surface of lumen 57. The cooperative engagement of the bottom contact surface of lumen 59 and lumen 57 provides a supplemental amount of securement in addition to that provided by seal 32 of valve apparatus 10a (see FIG. 5A). The user can then threadably couple the supplemental securement apparatus 50 to the valve apparatus 10*a* (see FIG. 5A) utilizing threaded coupler 46 of valve apparatus 10*a* (see FIG. 5A) and threaded coupler 58 of supplemental securement apparatus 50. Where the securement of the elongate instrument makes moving of the supplemental securement apparatus 50 relative to valve apparatus 10*a* (see FIG. 5A) difficult, the user can simply depress either lever arm 18 or release button 54 to draw valve apparatus 10*a* (see FIG. 5A) closer to supplemental securement apparatus 50 to allow coupling of threaded coupler 46 to threaded coupler 58.

As will be appreciated by those skilled in the art, a variety of types and configurations of supplemental securement apparatus can be provided without departing from the scope and spirit of the present invention. For example, according to one embodiment of the present invention, when the supplemental securement apparatus is coupled to the valve apparatus, toggling of the lever arm or other quick release actuator mechanism will release both the seal of the valve assembly and the engagement mechanism of the supplemental securement apparatus. According to another embodiment of the present invention, the supplemental securement apparatus is not removable from the valve apparatus. According to yet another embodiment of the present invention, the supplemental securement apparatus provides additional compressive forces on the existing seal rather than providing a secondary engagement mechanism. According to another embodiment of the present invention, the seal provides little or no gripping of the elongate instrument and the supplemental securement apparatus is provided to secure the elongate instrument relative to the valve apparatus. Securement apparatus 50 is one example of a supplemental engagement mechanism.

Figure 6A:
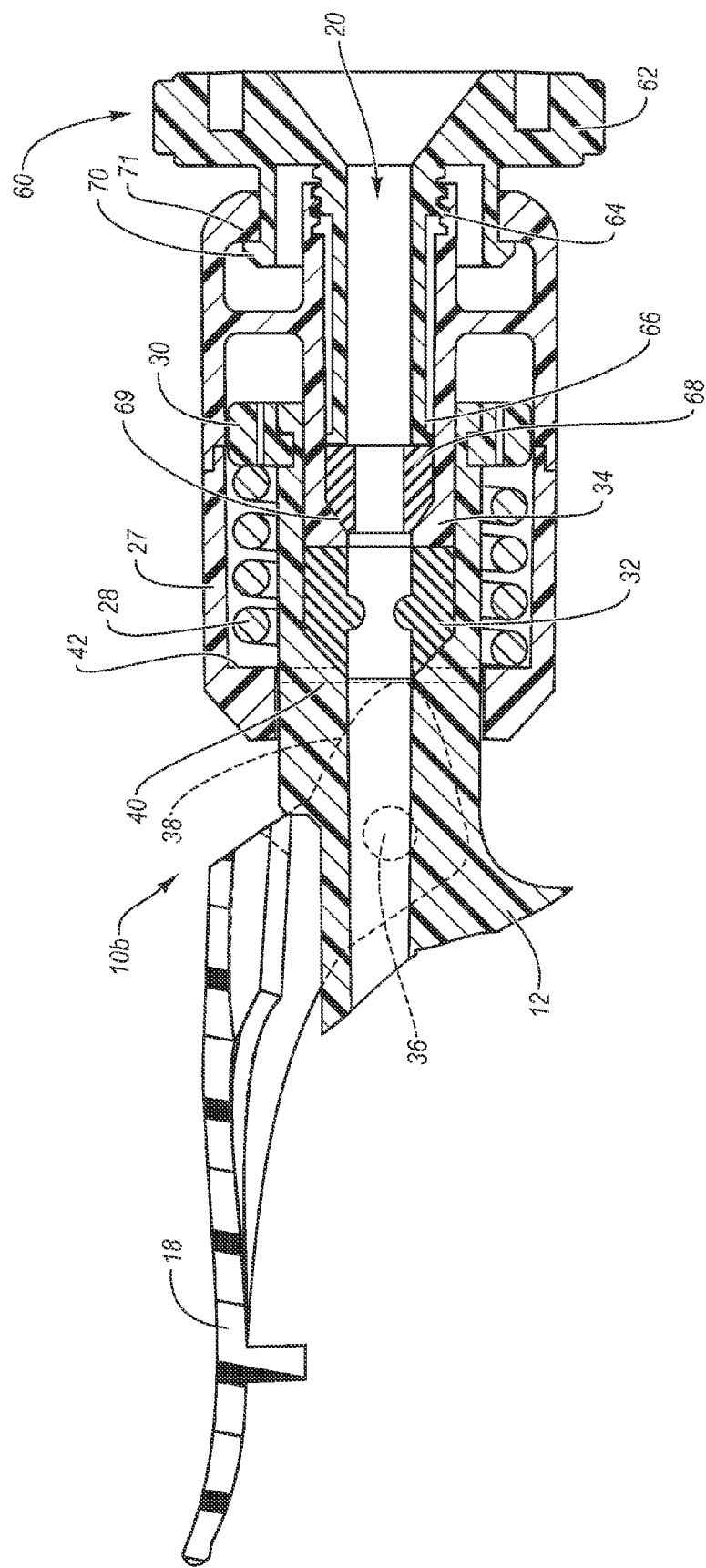
FIG. 6A is a side cross-sectional view of a valve apparatus having a supplemental securement valve assembly in which the seals of the valve apparatus are open.

FIG. 6A is a side cross-sectional view of a valve apparatus 10*b* according to one embodiment of the present invention. Valve apparatus 10*b* includes a valve assembly 16 and a supplemental securement valve assembly 60. In the illustrated embodiment, valve assembly 16 includes a housing 27. Spring 28 is positioned between a spring contact surface 42 of housing 27 and spring retainer 30. Lever arm 18 is depressed in a downward position such that the length of lever arm 18 is aligned with tubular body 12. As a result, housing 27 is biased in a proximal direction relative to tubular body 12. When housing 27 is biased in a proximal direction, plunger 34 is biased in a proximal direction and seal 32 is opened.

Supplemental securement valve assembly 60 is positioned at the proximal end of housing 27. In the illustrated embodiment, supplemental securement valve assembly 60 comprises a rotatable hub 62, threads 64, plunger 66, and a seal 68. Seal 68 is positioned within a seat 69 of housing 27. Seal 68 comprises a compressive seal which is similar to compressive seal 32 positioned within the seat of tubular body 12. Seat 69 has a tapered contact surface such that when a plunger exerts force on the proximal end of seal 68, the compressive forces result in closing of the lumen of compressive seal 68. Seal 68 is configured to be engaged by plunger 66. Rotatable hub 62 is utilized to urge plunger 66 in the direction of seal 68 and to exert compressive forces on seal 68. As a user exerts compressive forces on seal 68, seal 68 closes providing supplemental securement which is in addition to the securement provided by seal 32. By providing a seal 68 which is supplemental to seal 32, first and second securement points are provided in connection with an elongate instrument being utilized with valve apparatus 10*b*. In the illustrated embodiment, rotatable hub 62 has not been advanced and seal 68 is in an opened position. When seal 68 and seal 32 are in an opened position, a user can quickly and efficiently introduce medical instruments such as guidewires, catheters or other elongate tools through main lumen 20.

Figure 6B:
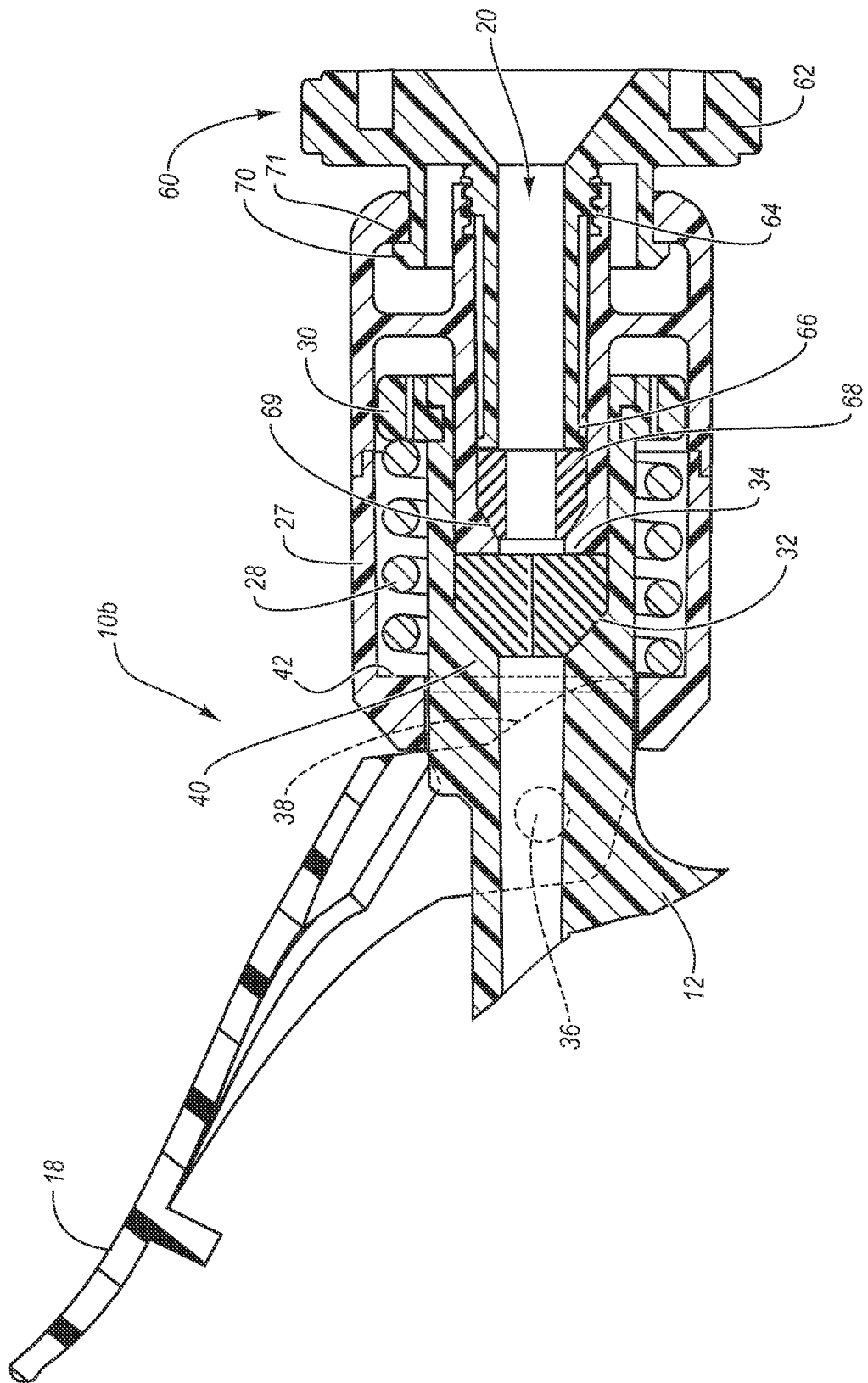
FIG. 6B is a side cross-sectional view of the valve apparatus of FIG. 6A in which one seal of the valve apparatus is in a closed position and one seal of the valve apparatus is in an opened position.

FIG. 6B is a side perspective view of the valve apparatus 10*b* of FIG. 6A. In the illustrated embodiment, a user has released lever arm 18 allowing lever arm 18 to return to a released configuration. As the user releases lever arm 18, the compressive forces exerted by spring 28 on housing 27 result in movement of housing 27 in the direction of lever arm 18. The movement of housing 27 is due to the compressive forces being exerted by spring 28 on annular spring contact surface 42 of housing 27. As housing 27 moves in the direction of lever arm 18, plunger 34 begins to exert a compressive force on the proximal end of seal 32. As plunger 34 begins to exert a compressive force on seal 32, seal 32 is sandwiched between the seat of tubular body 12 and plunger 34 and the central passageway 45 of seal 32 begins to close. In this manner, seal 32 prevents movement of an elongate surgical instrument position within lumen 20 while also preventing the passage of blood or other bodily fluids through main lumen 20 of valve apparatus 10.

In the illustrated embodiment, supplemental securement valve assembly 60 has not been actuated and seal 68 of the supplemental securement valve assembly 60 is opened. Seat 69 is positioned on the inside surface of plunger 34. In the illustrated embodiment, it can be seen that rotatable hub 62 is in a proximal position such that plunger 66 does not exert a compressive force on seal 68. While housing 27 advances the entire supplemental securement valve assembly 60 in a distal direction, the juxtaposition of the threads of rotatable hub 62 and housing 27 prevent plunger from exerting compressive forces on seal 68.

In the illustrated configuration, seal 32 provides a first amount of securement while also maintaining hemostasis when valve apparatus is in fluid communication with the vasculature of a patient. By having seal 32 closed and seal 68 opened, quick and simply opening of main lumen 62 can be effectuated by simply depressing lever arm 18 in a downward direction (see FIG. 6A). The combination of having seal 32 in a closed configuration and having seal 68 in an opened configuration can be advantageous during the insertion or removal of elongate instruments from main lumen 20. This can be particularly advantageous when additional gripping of the surgical instrument is not required.

Figure 6C:
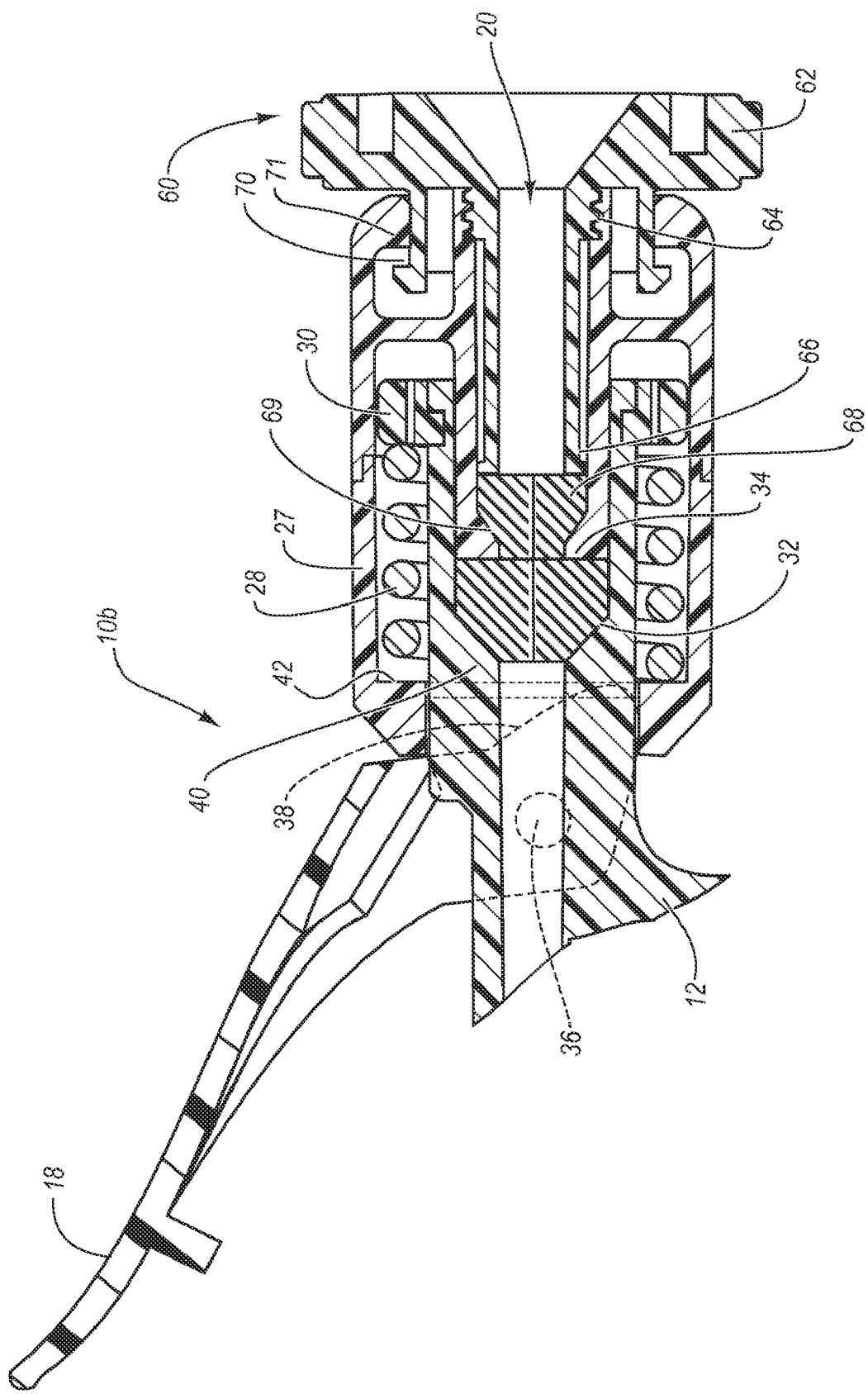
FIG. 6C is a side cross-sectional view of the valve apparatus of FIG. 6A in which the seals of the valve apparatus are in a closed position.

FIG. 6C is a perspective view of the hemostasis valve of FIGS. 6A and 6B illustrating seal 32 and seal 68 in a sealed position. In the illustrated embodiment, rotatable hub 62 has been advanced to close seal 68. The integral coupling of plunger 66 and rotatable hub 62 results in cooperative movement of rotatable hub 62 and plunger 66. In other words, as rotatable hub 62 advances, plunger 66 advances and engages seal 68. In this manner, a user can simply rotate rotatable hub 62 to close seal 68. Closing of seal 68 exerts a desired amount of compressive force which can secure an elongate instrument positioned along the length of main lumen 20. A retention flange 70 is provided in connection with rotatable hub 62. Retention flange 70 engages an annular flange 71 of housing 27. In this manner, as the user rotates rotatable hub 62 so as to decrease the compressive forces on seal 68, a maximum amount of releasing is provided. In other words, a stop point is provided which maintains the position of rotatable hub 62 relative to the other components of valve apparatus 10.

By providing a seal 68 which is supplemental to seal 32, first and second securement points are provided in connection with an elongate instrument being utilized with valve apparatus 10*b*. Seal 68 is one example of a supplemental securement mechanism. According to another embodiment, supplemental securement valve assembly 60 is one example of a supplemental securement mechanism. By providing first and second seals which can be utilized to secure an elongate instrument being utilized with valve apparatus 10b, a user can select a desired amount of pressure to be exerted in securing the elongate instrument relative to the valve apparatus. The ability to select variable amounts of pressure can be helpful to adapt the amount of securement to the variables of the operation being performed. For example, the size of the elongate instrument being utilized by the practitioner may require more or less securement pressure. Alternatively, the procedure with which the elongate instrument is being utilized may require additional securement to ensure that the elongate instrument does not move in a disadvantageous manner during the procedure being performed.

In the illustrated embodiment, a user has actuated supplemental securement valve assembly 60 to close seal 68 of the supplemental securement valve assembly 60. Seat 69 is positioned on the inside surface of plunger 34. In the illustrated embodiment, it can be seen that a user has rotated the rotatable hub 62 such that plunger 66 is exerting a compressive force on seal 68 in connection with seat 69 of housing 27. The rotation of rotatable hub 62 has moved the threads of the rotatable hub 62 relative to the threads of the body of housing 27. As a result, an amount of separation has been created between retention flange 70 and annular flange 71 of housing 27. In this manner, both seal 32 and seal 68 provide a desired amount of retention force in sealing of the main lumen 20 of valve apparatus 10b.

According to one embodiment of the present invention, a primary quick release mechanism can be utilized which will provide an initial amount of securement while also providing the bloodless exchange of such mechanism. Additionally, a secondary securement force can be provided to maintain the position of the instrument once the quick release portion of the procedure has been completed. The combination of a primary and secondary quick release mechanisms allows desired operability and greater flexibility in both sealing and securement of the elongate instrument during a procedure. Additionally, the operability of the valve apparatus is reliable, simple and efficient. The functionality provided by the valve apparatus can be particularly advantageous where particular portions of the procedure may require quick release and ease of operation while other portions of the procedure may require a greater amount of securement to prevent movement of the elongate instrument during the procedure. According to one embodiment of the present invention, the primary seal is normally closed while the supplemental securement apparatus is normally open.

Figure 7A:
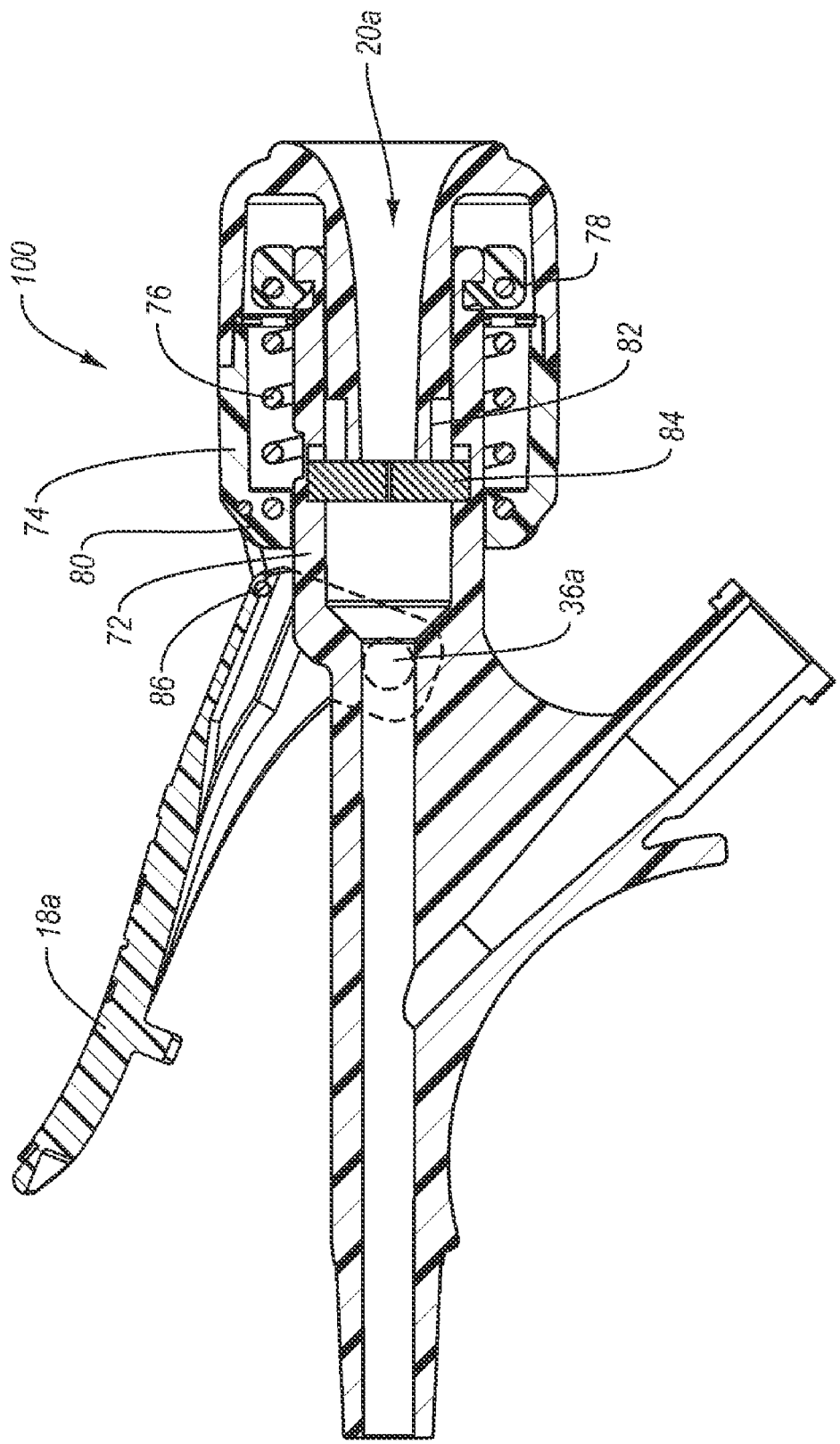
FIG. 7A is a side cross-sectional view of a valve apparatus having a non-compressible seal in which the seal is in a closed position.

FIG. 7A is a perspective view of a valve apparatus 100 according to one embodiment of the present invention. In the illustrated embodiment, valve apparatus 100 comprises a body 72, a lever arm 18A, a movable housing 74, a tension spring 76, and a non-compressible seal 84. In the illustrated embodiment, tension spring 76 is mounted to a spring mounting bracket 78 of body 72 and a spring mounting flange 80 of movable housing 74. Body 72 is secured to lever arm 18a by use of a pivot 36a. A linkage 86 connects lever arm 18a to movable housing 74. Tension spring 76 exerts a tensile force on movable housing 74 maintaining the position of movable housing 74 relative to body 72. In the illustrated embodiment, non-compressible seal 84 comprises a slit valve, bicuspid valve or tricuspid valve which is in a normally closed position.

When a user desires to open non-compressible seal 84, the user simply biases lever arm 18a in a downward direction. When the user biases lever arm 18a in the downward direction, lever arm 18a rotates downward about pivot 36A. As lever arm 18a moves in a downward direction, linkage 86 which is positioned between lever arm 18A and body 72 pulls movable housing 74 in a distal direction. The movement of movable housing 74 results in tensile forces being exerted on spring 76. Additionally, as movable housing 74 moves in the direction of lever arm 18a dilator 82 is advanced through the non-compressible seal 84.

Figure 7B:
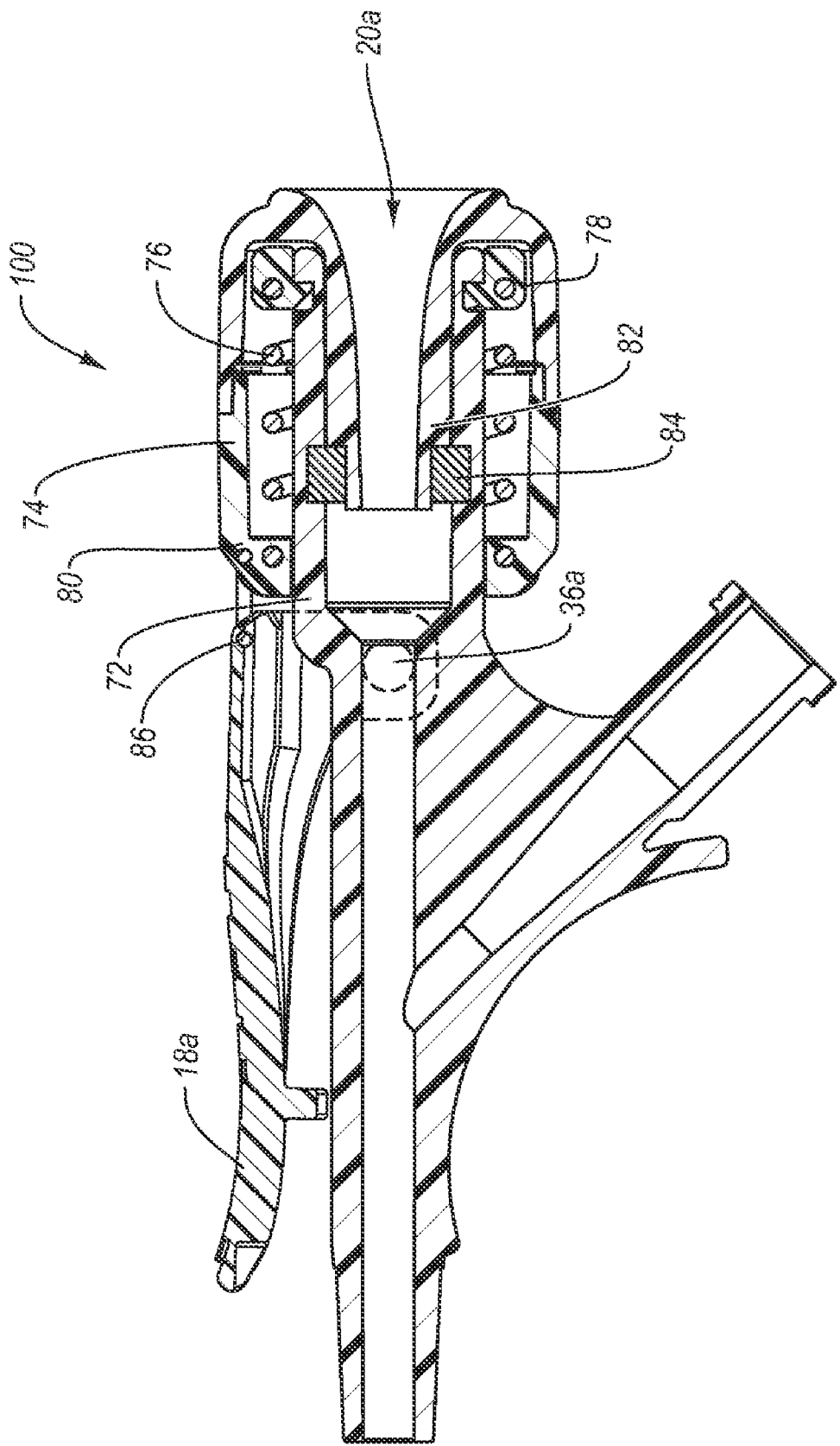
FIG. 7B is a side cross-sectional view of the valve apparatus of FIG. 7A illustrating a seal of the valve apparatus in an open position.

FIG. 7B illustrates lever arm 18a in a fully depressed position such that lever arm 18a is in alignment with the length of body 72. When lever arm 18a is fully depressed, movable housing 74 is positioned at its distal most displacement relative to the other components of valve apparatus 100. Additionally, dilator 82 is positioned at its distal most displacement. The distal end of dilator 82 is positioned through non-compressible seal 84 effectively opening the central passageway of non-compressible seal 84. When dilator 82 is positioned through the central aperture of non-compressible seal 84, a user can position an elongate instrument through non-compressible seal 84. In this manner, a user can simply and efficiently open and close the non-compressible seal to provide a simple and easy access through main lumen 20A of the valve apparatus 100. When a user releases the downward force exerted on lever arm 18A, the tensile forces provided by tension spring 76 pulls spring mounting flange 80 of body 72 in the direction of spring mounting bracket 78. As a result, dilator 82 is retracted from non-compressible seal 84 allowing non-compressible seal 84 to close and return to the configuration depicted in FIG. 7A.

As will be appreciated by those skilled in the art, a variety of types and configurations of valve apparatus can be provided without departing from the scope and spirit of the present invention, for example, according to one embodiment of the present invention, the dilator and non-compressible seal are utilized with resilient seals that are not slit valves, bicuspid valves, or tricuspid valves. In another embodiment, a non-compressible seal is utilized without a dilator. According to another embodiment of the present invention, a securement apparatus separate from the seal is provided. According to another embodiment of the present invention, a compressive spring is utilized to actuate or deactuate the quick release mechanism. According to another embodiment of the present invention, a bi-stable mechanism is provided which allows a user to toggle between opened and closed positions. According to another embodiment of the present invention, a compressive spring is provided to actuate or deactuate the mechanism. According to yet another embodiment of the present invention, a user exerts forces directly on the housing rather than by using a secondary release mechanism.

Figure 8:
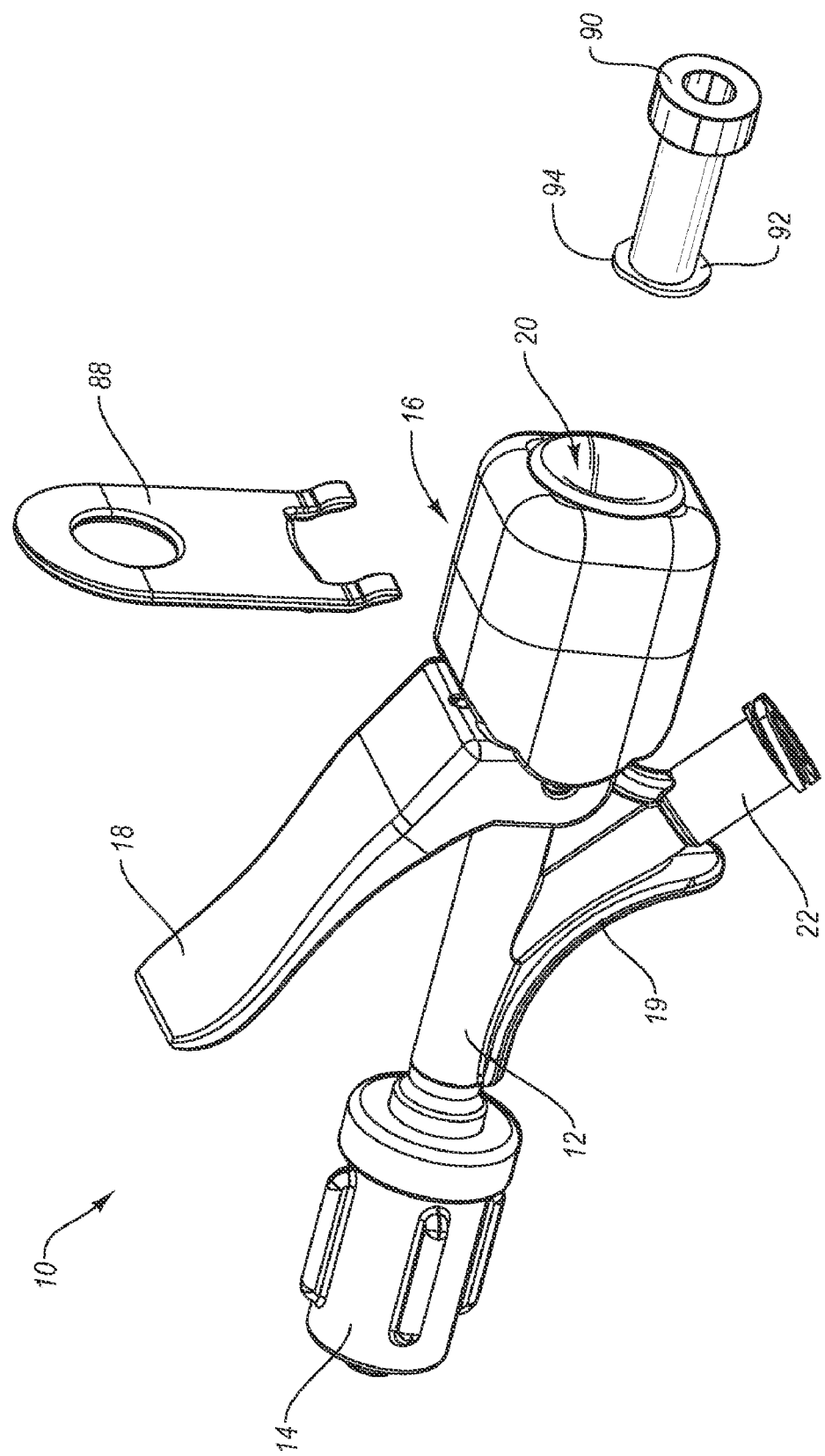
FIG. 8 is a perspective view of a valve apparatus having a relief member and seal actuator which relieve pressure on the seal of the valve apparatus during shipping and/or storage of the valve apparatus.

FIG. 8 is a perspective view of valve apparatus 10 according to one embodiment of the present invention. In the illustrated embodiment, valve apparatus 10 includes a relief member 88 and a seal actuator 90. Relief member 88 and seal actuator 90 are configured to maintain the integrity of the valve apparatus seal during storage and shipment of valve apparatus 10. Relief member 88 is configured to be positioned between lever arm 18 and valve assembly 16. Relief member 88 is adapted to prevent lever arm from moving to a fully released position. As a result, lever arm 18 does not move the components of valve assembly in a manner that will exert a full compressive force on the seal associated with valve assembly 16. Thus, during storage, the compressive seal is in a more relaxed state which reduces fatigue that could minimize the effectiveness of the seal once the seal is utilized during operation.

Seal actuator 90 is positioned within main lumen 20 of valve apparatus 20. Seal actuator 90 is positioned within the valve assembly 16 in a manner such that a shaft 92 of the seal actuator 90 is positioned within the lumen of the seal associated with valve assembly 16. As a result, shaft 92 of the seal actuator 90 also helps to limit fatigue on the seal positioned within valve assembly 16.

When a user removes valve apparatus 10 from the packaging, the user simply exerts a depressive force on lever arm 18 and removes relief member 88 from the position between lever arm 18 and valve assembly 16. Similarly, seal actuator 90 is grasped and removed from main lumen 20. An annular flange 94 is positioned on the proximal end of shaft 92 such that when seal actuator 90 is removed from lumen 20, the annular flange will engage the seal and result in full actuation of the seal.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A valve apparatus comprising:
   a body having a lumen therethrough and which is configured to access the cardiovascular or other intravenous system of a patient;
   a compressible seal having a longitudinal passageway therethrough which communicates with the lumen and provides access thereto, wherein the seal is adapted to be selectively actuatable to seal or unseal the lumen,
   a quick release actuator mechanism, for selectively allowing the user to actuate the seal to seal or unseal the lumen of the body, wherein the quick release actuator comprises a compression spring which provides a compressive force to a plunger which exerts a compressive force on the seal to close the longitudinal passageway, and wherein the quick release actuator mechanism allows the user to access the lumen of the valve apparatus when the quick release actuator mechanism is in a sealed position and an unsealed position,
   a relief member removably disposed between the quick release actuator mechanism and the seal, the relief member configured to prevent complete compression of the seal when the relief member is disposed between the quick release actuator mechanism and the seal.

2. The valve apparatus of claim 1, wherein the quick release actuator mechanism comprises a lever arm.

3. The valve apparatus of claim 2 wherein the lever arm has an upper surface, the upper surface having a textured portion configured to provide a gripping texture on the upper surface.

4. The valve apparatus of claim 1, wherein the compression spring is compressed substantially parallel to the direction of movement of plunger.

5. The valve apparatus of claim 1, further comprising a seal actuator having a shaft removably disposed within the longitudinal passageway of the seal.

6. The valve apparatus of claim 5, wherein the seal actuator has an annular flange configured to engage the seal when the seal actuator is removed from the longitudinal passageway.

7. The valve apparatus of claim 1, wherein the body has a finger support.

8. The valve apparatus of claim 1 wherein the relief member has a flange configured to contact the quick release actuator mechanism.

9. The valve apparatus of claim 1 wherein a portion of the relief member is configured to be directly graspable by a user.

* * * * *